United States Patent
Hoctor et al.

(10) Patent No.: US 8,388,544 B2
(45) Date of Patent: Mar. 5, 2013

(54) SYSTEM AND METHOD FOR MEASURING BLOOD VISCOSITY

(75) Inventors: Ralph Thomas Hoctor, Saratoga Springs, NY (US); Aaron Mark Dentinger, Latham, NY (US)

(73) Assignee: General Electric Company, Niskayuna, NY (US)

( * ) Notice: Subject to any disclaimer, the term of this patent is extended or adjusted under 35 U.S.C. 154(b) by 1739 days.

(21) Appl. No.: 11/669,602

(22) Filed: Jan. 31, 2007

(65) Prior Publication Data
US 2007/0123779 A1 May 31, 2007

Related U.S. Application Data (63) Continuation-in-part of application No. 11/083,259, filed on Mar. 17, 2005, now Pat. No. 7,621,876.

(51) Int. Cl.
*A61B 5/02* (2006.01)
*A61B 8/00* (2006.01)

(52) U.S. Cl. .................................................. 600/504

(58) Field of Classification Search .......... 600/472–481, 600/483–486, 488, 500–508
See application file for complete search history.

(56) References Cited

U.S. PATENT DOCUMENTS

| | | | |
|---|---|---|---|
| 3,760,384 | A | 9/1973 | Krolikowski et al. |
| 4,679,302 | A | 7/1987 | Theriault et al. |
| 6,362,028 | B1 | 3/2002 | Chen et al. |
| 2006/0184026 | A1 | 8/2006 | Nakamura et al. |
| 2006/0211942 | A1 | 9/2006 | Hoctor et al. |
| 2006/0241459 | A1 | 10/2006 | Tai |

OTHER PUBLICATIONS

C. Cohen-Bacrie, "Estimation of Viscosity From Ultrasound Measurements of Velocity Profiles", 1999 IEEE Ultrasonics Symposium, pp. 1489-1492.
W. R. Milnor, M.D., "Hemodynamics", 2nd Edition, Williams & Wilkins, 1989, pp. 126-132.
R. G. Brown, "Introduction to Random Signal Analysis and Kalman Filtering", John Wiley & Sons, 1983, pp. 302-307.

*Primary Examiner* — Navin Natnithithadha
(74) *Attorney, Agent, or Firm* — Marie-Claire B. Maple

(57) ABSTRACT

A technique is provided for computing or monitoring blood viscosity. The technique includes measuring a cross sectional area of a arterial segment and a volumetric flow rate of blood flowing through the arterial segment at two or more locations, estimating a compliance transfer function from blood measurements to scale the arterial cross sectional area into a pressure waveform, deriving a transmission line model of the arterial segment based on the cross sectional area, as scaled by the compliance transfer function, of the arterial segment at the two or more locations and the volumetric flow rate of blood at the two or more locations. The technique also includes computing the blood viscosity based on the transmission line model.

29 Claims, 4 Drawing Sheets

SYSTEM AND METHOD FOR MEASURING BLOOD VISCOSITY

CROSS REFERENCE TO RELATED APPLICATIONS

This application is a Continuation-in-Part of U.S. patent application Ser. No. 11/083,259, entitled "CONTINUOUS, NON-INVASIVE TECHNIQUE FOR DETERMINING BLOOD PRESSURE USING A TRANSMISSION LINE MODEL AND TRANSCUTANEOUS ULTRASOUND MEASUREMENTS", by Ralph T. Hoctor et al. filed on Mar. 17, 2005, which is herein incorporated by reference.

BACKGROUND

The invention relates generally to a technique of measuring blood viscosity, and more particularly to a non-invasive technique of measuring blood viscosity using an arterial transmission line model.

Blood viscosity is an important physiological parameter for evaluating the condition of a patient. For example, blood viscosity is indicative of the hematocrit level of the patient. It is also helpful in predicting diseases such as diabetes, hypertension, infections, and infarctions. Additionally, it is of interest to monitor blood viscosity in the patient receiving antiplatelet drugs. Traditional techniques for ex-vivo measurement of blood viscosity employ a tube viscometer or a rotational viscometer. However, these techniques require drawing blood from the patient by making an incision into the patient's skin. This invasive procedure is complicated, painful, and therefore undesirable to the patient.

Certain non-invasive techniques for measurement of blood viscosity have been proposed. These techniques estimate the blood viscosity from the blood flow profile measured by an ultrasound flow meter. However, these techniques may not provide accurate measurement of the blood viscosity, as the parameters governing the viscosity measurement are themselves susceptible to measurement errors on account of various factors such as changes in the physiological state of the patient, elastic nature of the arterial, technique employed to measure the respective parameter, and so forth.

It is therefore desirable to provide a more accurate and non-invasive blood viscosity measurement technique.

BRIEF DESCRIPTION

Briefly, in accordance with one aspect of the technique, a method is provided for computing or monitoring blood viscosity. The method provides for measuring a cross sectional area of an arterial segment and a volumetric flow rate of blood flowing through the arterial segment at two or more locations, estimating a compliance transfer function for the arterial segment using measured minimum, maximum and mean values of blood pressure, and deriving a transmission line model of the arterial segment based on the cross sectional area of the arterial segment at the two or more locations, as scaled by the compliance transfer function, and the volumetric flow rate of blood at the two or more locations. The method also provides for computing the blood viscosity based on the transmission line model. Systems and computer programs that afford such functionality may be provided by the present technique.

In accordance with another aspect of the technique, a method is provided for computing or monitoring blood viscosity. The method provides for measuring a cross sectional area of a arterial segment and a volumetric flow rate of blood flowing through the arterial segment via an ultrasound sensor at two or more locations, estimating a compliance transfer function for the arterial segment using measured minimum, maximum and mean values of blood pressure, and deriving a transmission line model of the arterial segment. The transmission line model includes a ladder network comprising a plurality of RLC stages between an input current source and an output current source. Each of the plurality of RLC stages further includes a series resistor, an inductor, and a capacitor. The input current source is a volumetric flow rate of blood entering the arterial segment, the output current source is a volumetric flow rate of blood leaving the arterial segment, resistance of the series resistor is analogous to the resistance of the arterial segment and is given by $R=8\eta/\pi r^4$, inductance of the inductor is analogous to the inertance of the blood in the arterial segment and is given by $L=\rho/\pi r^2$, and capacitance of the capacitor is analogous to the compliance of the arterial segment and is given by $C=dA/dP$, wherein $\eta$ is the blood viscosity, $\rho$ is the blood density, $r$ is the radius of the arterial segment, $A$ is the area of the arterial segment, and $P$ is the blood pressure. The method also provides for using the transmission line model in a computational method to determine resistance of each of the series resistors, and computing the blood viscosity from the resistance. Here again, systems and computer programs affording such functionality may be provided by the present technique.

In accordance with a further aspect of the technique, a method is provided for computing or monitoring blood viscosity. The method provides for measuring a cross sectional area or a diameter of an arterial segment and a volumetric flow rate of blood flowing through the arterial segment via an ultrasound sensor at two or more locations, and measuring a peak systolic, a minimum diastolic and a mean blood pressure via a blood pressure cuff using the standard oscillometric method, to generate an estimated compliance function. The method also provides for computing an inertance of the blood contained in the arterial segment based on a known density of blood and the time-varying diameter of the segment, inputting the volumetric flow rate of blood entering the arterial segment, the volumetric flow rate of blood leaving the segment, and the area or radius of the arterial segment into a Kalman filter, determining a resistance of the arterial segment that minimizes a prediction error, and computing the blood viscosity from the resistance in the arterial segment. The prediction error is the total difference between the prediction of the state variables of the Kalman filter for a given resistance and the measured values of the state variables. Here again, systems and computer programs affording such functionality may be provided by the present technique.

In accordance with an additional aspect of the technique, a blood viscosity measurement and monitoring system is provided. The system includes two or more ultrasound sensors configured to measure a cross sectional area of an arterial segment and a volumetric flow rate of blood flowing through the segment at two or more locations respectively. The system also includes a blood pressure cuff configured to measure a blood volume in the limb (arm or leg) segment to generate an estimated compliance curve, and a processor coupled to the two or more ultrasound sensors and the blood pressure cuff and configured to derive a transmission line model of the arterial segment based on the cross sectional area of the arterial segment at the two or more locations, and the volumetric flow rate of blood at the two or more locations, and to compute the blood viscosity based on the waveforms produced by the transmission line model.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
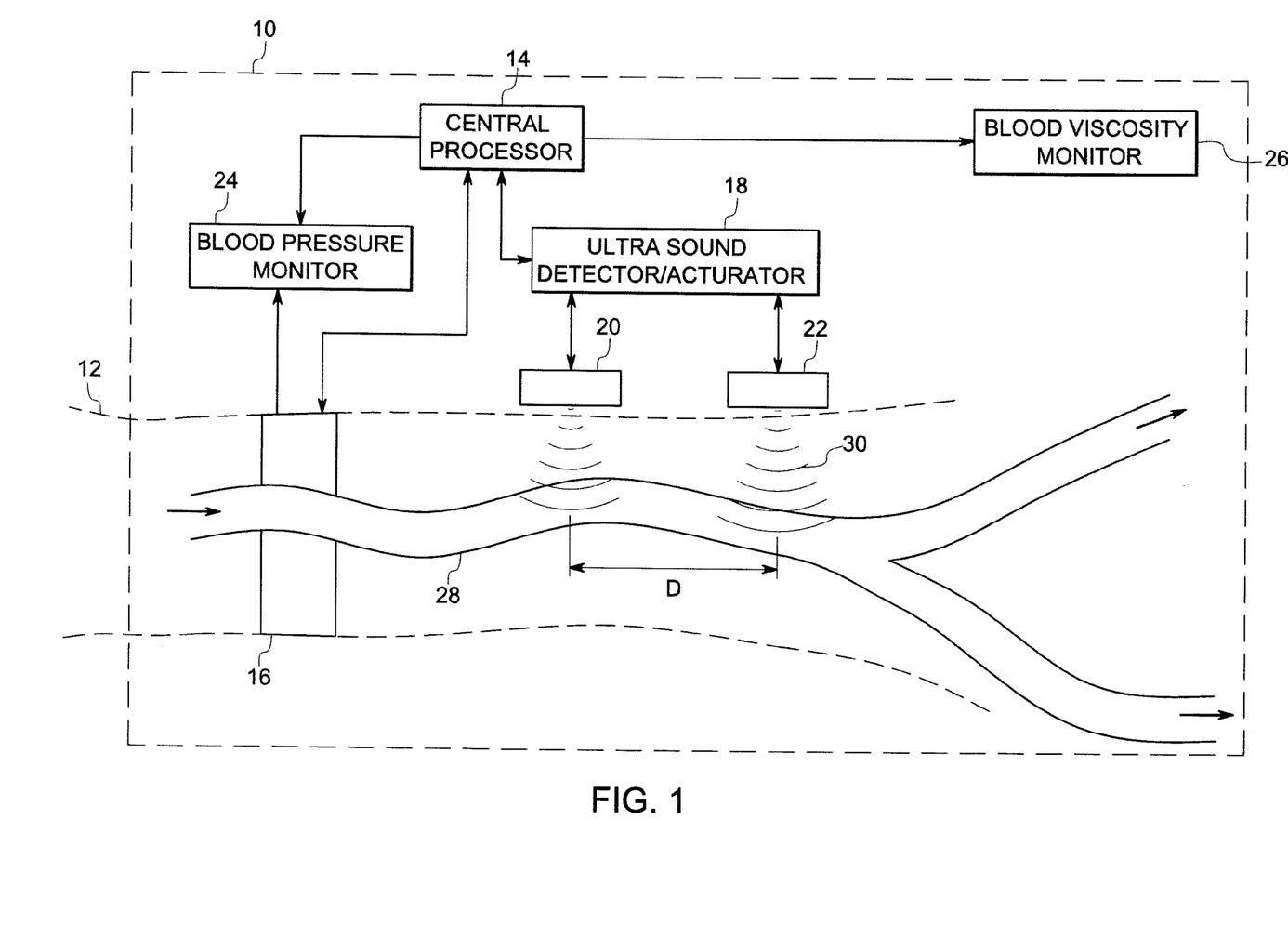
FIG. 1 depicts a blood viscosity measurement and monitoring system in accordance with one aspect of the present technique.

Referring now to FIG. 1, a blood viscosity measurement and monitoring system 10 is illustrated in accordance with aspects of the present technique. As will be appreciated by one skilled in the art, in certain embodiments, the blood viscosity measurement and monitoring system 10 may be part of an overall patient monitoring system that may provide medical personnel with information regarding different physiological parameters of a patient 12. The patient monitoring system may additionally include an electrocardiograph (ECG), a pulse oximeter, and a blood pressure measurement and monitoring system.

In the co-pending application Ser. No. 11/083,259, a method for continuous, noninvasive blood pressure estimation is taught that uses a very similar signal processing approach to that of the present invention. In that invention, the blood pressure estimation algorithm is occasionally re-calibrated by inflating the blood pressure cuff, and during these re-calibrations, the blood viscosity estimation method of the present invention can be performed, using the same system taught in Ser. No. 11/083,259.

The blood viscosity measurement and monitoring system 10 includes a central processor 14, such as digital signal processor (DSP), configured to perform blood viscosity measurement and monitoring functions as will be described in greater detail below. The central processor 14 is coupled to a conventional blood pressure cuff 16 and to ultrasound activation and detection circuitry 18, which in turn is coupled to two or more ultrasound patch probes or sensors 20, 22. A display device 24 may be coupled to the blood pressure cuff 16 to display the measured blood pressure of the patient 12 (i.e., the readings taken by the blood pressure cuff 16). The display device 24 may also be coupled to the central processor 14 to display the measured blood pressure of the patient 12. Additionally, another display device 26 may be coupled to the central processor 14 to display the blood viscosity of the patient 12. As will be appreciated by one skilled in the art, the central processor 14, the blood pressure cuff 16, the ultrasound and activation detection circuitry 18, the ultrasound probes 20, 22, the blood pressure display device 24, and the blood viscosity display device 26 may be coupled to each other over a wired or a wireless communication link.

The blood pressure cuff 16 is configured to measure blood pressure of the arterial segment. The blood pressure cuff 16 may be positioned around the arm of a patient and can be operated in the conventional manner, using the oscillometric approach, to obtain actual systolic, diastolic and mean blood pressure readings from the patient 12. The device then uses these three numbers to scale the area waveforms obtained using the ultrasound probes over a period of time including multiple heart cycles. The function used for this scaling operation is called a compliance curve. For example, a simple compliance curve can be obtained by averaging the minimum, and maximum values of the arterial area over all the observed heart cycles and averaging all the areas over the save period of time. A simple, piecewise linear compliance curve can be constructed by linearly interpolating instantaneous values of the area that fall between two of the three known values. Alternatively, a second-order polynomial could be fit to the three pairs of values: (min area, min pressure), (mean area, mean pressure) and (max area, max pressure), yielding an expression for pressure as a quadratic polynomial function of the instantaneous area.

The two or more ultrasound patch probes or sensors 20, 22 are configured to measure an area of an arterial segment 28 and a volumetric flow rate of blood flowing through the segment 28 at two or more locations respectively. As will be appreciated by one skilled in the art, in certain embodiments, the ultrasound patch probes 20, 22 may be configured to measure a radius or a diameter of the arterial segment 28. In such cases the area of the arterial segment 28 may be estimated from the diameter or the radius. As illustrated in FIG. 1, the first ultrasound patch probe 20 and the second ultrasound patch probe 22 are spaced apart from each other by a distance D along the upper arm of the patient 14. Further, it should be noted that each of the ultrasound patch probes 20, 22 is positioned on the arm of the patient in such a manner as to enable transcutaneous insonification of an artery. Each of the ultrasound patch probes 20, 22 is positioned generally above the brachial artery of the patient. Likewise, the blood pressure cuff 16 is positioned to sense blood pressure in the brachial artery of the patient. Although the first and second ultrasound patch probes 20, 22 are shown positioned along the upper arm of the patient 12, it should be understood that the ultrasound probes 20, 22 could be positioned on any unbifurcated, superficial arterial segment in the patient's body. For example, the ultrasound patch probes 20, 22 and the blood pressure cuff 16 may be positioned above the femoral artery.

The use of transcutaneous ultrasound can provide volumetric flow and arterial lumen area (cross sectional area of the arterial segment). In addition, ultrasound measurements can be taken in such a way that all the data describes a single, uniform arterial segment (e.g., the brachial can be used), and such blood flow or blood volume as exists in nearby veins can be ignored. As will be appreciated by one skilled in the art, in certain embodiments, software may be employed to automatically locate the artery in the ultrasound data by using known edge detection techniques or other such techniques. Arteries can be automatically distinguished from veins using well-known Doppler blood flow techniques to locate those arterials with pulsitile flow. Autonomous operation of the ultrasound system allows it to report blood viscosity and blood flow traces to the clinical users without those users having to interpret an ultrasound image or to operate an ultrasound imaging device.

The use of ultrasound measurements in the continuous non-invasive blood viscosity monitoring applications is enabled by micromachined ultrasonic transducer patch probe technology, which allows ultrasound data to be taken using a thin, lightweight probe that adheres to the patient's skin. The micromachined ultrasonic transducers (MUTs) may be of the capacitive (cMUT) variety or piezoelectric (PMUT) variety. The use of a MUT patch allows a clinician to attach the transducer to the patient's skin, as the MUT patch is lightweight and flat. As will be appreciated by one skilled in the art, cMUTs are tiny diaphragm-like devices with electrodes that convert the sound vibration of a received ultrasound signal into a modulated capacitance. For transmission, the capacitive charge is modulated to vibrate the diaphragm of the device and thereby transmit a sound wave. Similarly, pMUTs are tiny devices based on piezoceramic elements for transmission and reception of ultrasound signals.

Additionally, it should be noted that the present technique encompasses not only a device, but also methods for continuous non-invasive blood viscosity monitoring, and that the basic method is not limited to devices that employ MUT technology. Instead, the basic method disclosed herein can also be performed by appropriately programmed ultrasound imaging systems having probes comprising conventional piezoceramic transducer elements.

Based on acoustic data from the ultrasound patch probes 20, 22 and pressure data from the blood pressure cuff 16, the processor 14 autonomously computes various parameters, including the patient's estimated blood viscosity. In addition, the processor software forms and steers ultrasound beams over the volume of space in front of the ultrasound patch probes 20 and 22. Using both echo intensity and Doppler blood flow information, the software maps out the location of the vessel, its cross-sectional area, and the volumetric flow.

For the continuous non-invasive blood viscosity measurement and monitoring applications, two types of data are acquired simultaneously using the ultrasound sensors. The first data type is a sequence of B-mode images providing several short-axis views of the artery (in planes perpendicular to the direction of blood flow). Two or more short-axis views are taken along the length of the artery. The center of the artery can be found at each measurement location using edge detection techniques. The center of the artery can then be estimated for any location under the blood pressure cuff using interpolation. In addition to finding the artery center, the B-mode data is used to estimate the vessel diameter for arterial area calculations. More specifically, it is assumed that the cross section of the lumen is a circle, so the estimated diameter can be used to calculate the lumen area A. Alternatively, in a short-axis B-mode image with a sufficiently high line density, the area may be computed directly from the image, either before or after scan conversion.

The second data type is a set of M-mode lines to be used for Doppler processing. The M-mode lines remain locked onto the center of the artery using information from the B-mode data. The multiple M-mode lines can be used with a Doppler steering angle for determining blood velocities. Since one requires volumetric flow information in the model, one needs to integrate the flow rate over the area of the vessel lumen. There are two ways that this can be done. Both methods require a multi-gate, pulsed Doppler system that forms mean Doppler frequency shift estimates at multiple points along the ultrasound look direction. In the first approach, only a single line of such estimates is formed, directed through the center of the vessel. The required volumetric flow is obtained by assuming that the vessel cross-section is round and that the flow profile is rotationally symmetric. This is the approach that corresponds to color M-mode, as will be described in greater detail below. However, this approach results in a biased approximation in some cases. The second approach is to measure the Doppler frequency shift along several ultrasound lines that together cover the vessel lumen. The flows are all associated with some small patch of the lumen cross-section and an approximate spatial integral of the flow is formed by multiplying each flow value by the area of the associated patch and summing.

The two types of data are acquired by interleaving the acquisitions of the short-axis B-mode beams and the Doppler M-mode beams. A repeating scan sequence consists of a single B-mode beam at each location and all the M-mode beams. In the next pass through the sequence, the B-mode beams are translated across the patch while the M-mode beams remain in the same position. This is repeated until the desired width for the B-mode image is covered, generating a single frame of the B-mode data. Then the steps are repeated using any updated information about the vessel center. The result of the acquisition is M-mode data at a high repetition rate (~2 kHz), as required for Doppler processing, and the B-mode images at a slower rate (~100 Hz) determined by the required image size for vessel tracking.

The B-mode beams are translated across the ultrasound sensors by translating an aperture of the planer array (e.g., annular array) of activated sub-elements across the patch. A uniform translation of the beamforming coefficients produces a new beam at a different location. Repeated frequently, this generates a rectilinear two-dimensional image. An additional delay imposed across the active aperture produces a beam directed away from the normal. Such beams are transmitted in the M mode to acquire data for Doppler processing that computes the blood velocity based on the Doppler effect.

Referring back to FIG. 1, each of the first and second ultrasound patch probes 20, 22 can be actuated by the activation circuitry 18 to emit an ultrasound pulse 30. The sequence of ultrasound pulses 30 enables multiple measurements and determinations of various parameters of a uniform stretch of the arterial segment 28, such as the brachial artery, positioned between each of the ultrasound patch probes 20, 22. In the illustrated embodiment, the ultrasound patch probes 20, 22 are shown spaced over a length of the unbifurcated brachial artery. Specifically, the central processors 14 can determine the internal area of the artery at the location beneath the first ultrasound patch probe 20 and at the location beneath the second ultrasound patch probe 22. In addition to determining the area of the artery 28, the central processor 14 can utilize the Doppler ultrasound flow measurement technique to determine the instantaneous flow of blood at a first location beneath the first ultrasound patch probe 20 and at a second location beneath the second ultrasound patch probe 22. Thus, the central processor 14, through the ultrasound activation circuit 18 and the pair of ultrasound patch probes 20, 22 can determine the arterial area and blood flow rate at two separate locations along the radial artery which are spaced by the distance D. These two measurements made through the use of the ultrasound patch probes 20, 22 provide important and accurate information to the central processor 14 that aids in the determination of a continuous, non-invasive blood viscosity measurement as described in detail below. Alternatively, in certain embodiments, the patch probes 20, 22 can be spaced over a range of the arterial segment having several bifurcations. However, this requires additional measurements. For example, in order to be able to practice this variant of the present technique, one should know how far along the segment the bifurcation occurred. Moreover, the blood flow rate and area of the arterial segment in all of the bifurcated branches needs to be measured.

The data processing scheme associated with the present technique requires that at least two ultrasound probes be deployed along the length of a short arterial segment. Each of these probes must have a steerable beam and must be able to operate at an angle with respect to the skin normal so that it can collect Doppler blood flow measurements. Such a probe can also be steered to the normal angle and used to measure the area of the artery's lumen. As will be appreciated by one skilled in the art, additional probes may be employed between the two end probes, all of them at known locations along the line of the arterial segment.

Figure 2:
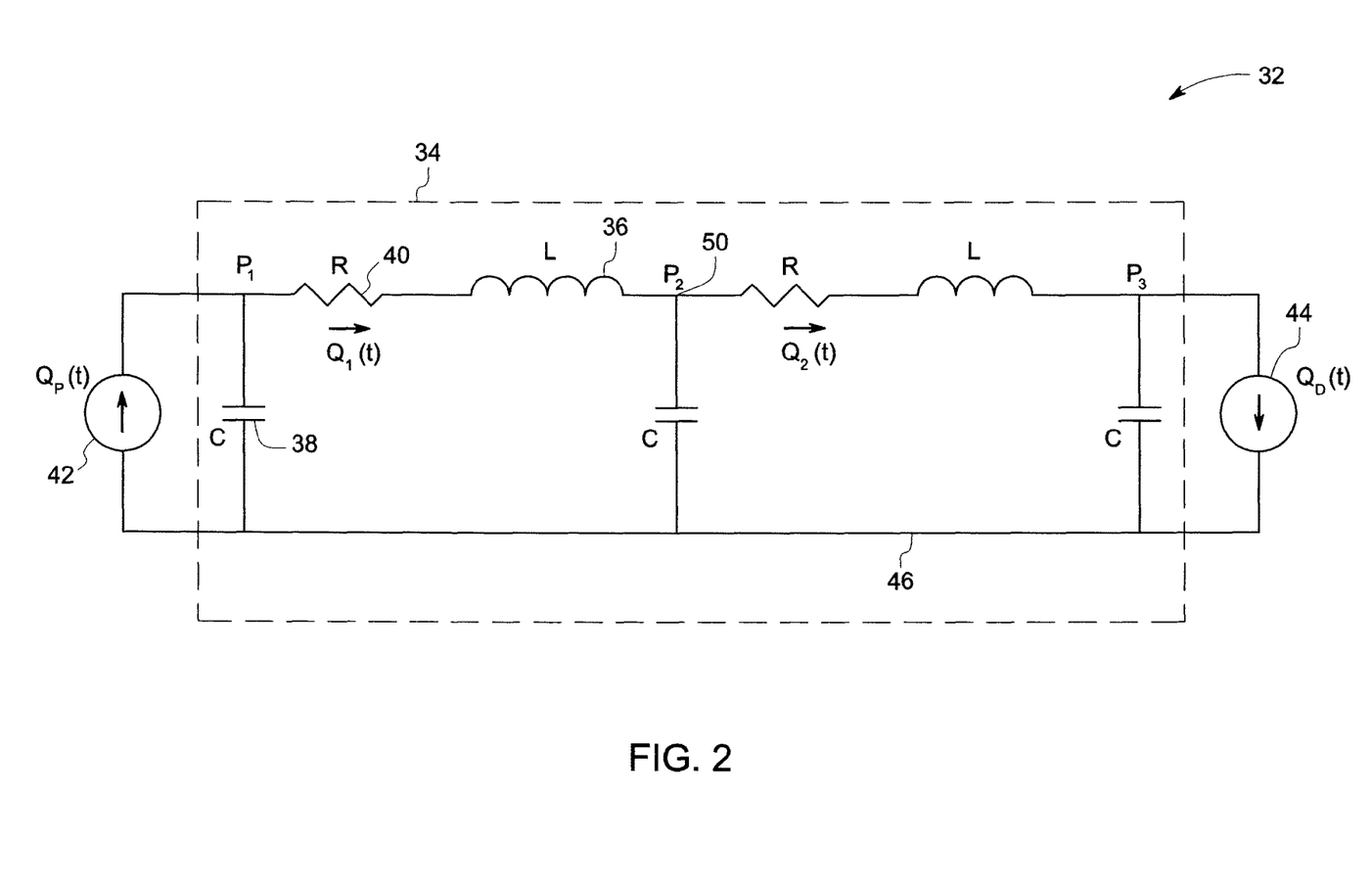
FIG. 2 depicts a schematic of the transmission line model utilized to measure the blood viscosity of the arterial segment in accordance with aspect of the present technique.

The blood viscosity measurement and monitoring system 10 utilizes an algorithm in which a length of an unbifurcated arterial segment is represented by a transmission line model 32 as illustrated in FIG. 2. The use of transmission line model to represent the arterial segment is described in *Hemodynamics, 2nd edition*, pages 126-132, by W. R. Milnor, published by Williams & Wilkins, 1989, the entirety of which is hereby incorporated by reference herein. As will be appreciated by one skilled in the art, the transmission line model 32 is generally used for determining the phase velocity of electrical waves propagating in a cable or transmission line. In accordance with the present technique, the transmission line model 32 can be analogized to the flow of blood in a distensible tube (arterial segment), and thus used to make blood pressure and viscosity measurements. In the present technique, the transmission line is an analog for such a tube, with electric charge corresponding to fluid volume, current corresponding to volumetric flow and voltage corresponding to pressure. Thus, the specified flow measurements are like direct measurements of current in the analogous electric circuit.

In accordance with the present technique, the transmission line model 32 is represented by a ladder network 34 having multiple stages. Each stage of the ladder network represents a short sub-segment of the arterial segment. The operation of this network may be represented by a set of simultaneous, first-order differential equations, which may be used to derive a discrete-time state variable model for the system, given a sample rate. In the state variable model, half of the state variables will be pressures, the other half will be volumetric flows. This model can then be driven by ultrasound measurements and the pressure estimate will be given by one of the pressure state variables. Naturally, the model must have parameters that accurately represent the physical system in order to give meaningful results.

The general method of allowing a state variable model to evolve in time is reminiscent of the numerical solution of an initial value problem using Euler's method. The present apparatus approach differs from a typical initial value problem in that the equation to be solved is inhomogeneous, so if the system is stable, the particular solution associated with the driving function dominates the general solution. It is for this reason that any unknown initial values of the state variables may be ignored.

The transmission line model 32 is represented in the signal processing method as a RLC lossless ladder network shown in FIG. 2. In the present application, the term "lossless" indicates that no mass (i.e. blood) is lost from the input to the output of the network, such as in a length of an unbifurcated arterial segment. The analogous quantity to the inductance L of the ladder network is the mass per unit length (per ladder network section) and the analogous quantity to the capacitance C is the elastic compliance of the tube. The resistors R represent energy loss due to the viscosity of blood. In the simplest version, the network is driven at both ends by current sources, representing the volumetric blood flow measurements derived from ultrasound. Although the RLC ladder network in FIG. 2 is described as being a "lossless" network, it should be noted that if the present technique is used on bifurcated arterial segment, such as the radial artery, the transmission line model needs to be modified to reflect the bifurcation geometry and that all flow into and out of the bifurcated segment must be measured.

In the embodiment illustrated in FIG. 2, the transmission line model includes an RLC ladder network 34 having multiple stages. Each of the multiple RLC ladder network stages further includes an inductor (L) 36, a capacitor (C) 38 and a series resistor (R) 40. The transmission line model further includes current sources 42 and 44 at both ends of the RLC ladder network.

In practice, the order of the transmission line model, which is related to the number of serial sections employed, is to be determined by the length of the arterial segment to be modeled, and the parameters represent values of an underlying distributed parameter, expressed per length of the individual section. For example, if the distance between the proximal and distal flow measurements is 5 cm (which is typical), then a 10-section transmission line model would have its compliance value given in units equivalent to "compliance per 5 mm section of tube". When the length of the individual section is short enough, then the compliance value in the model gives an approximate relationship between area and pressure.

The operation of the network of FIG. 2 is expressed via the following set of simultaneous ordinary differential equations:

$$Q_P - Q_1 = C\,dP_1/dt$$

$$P_1 - P_2 = RQ_1 + L\,dQ_1/dt$$

$$Q_1 - Q_2 = C\,dP_2/dt$$

$$P_2 - P_3 = RQ_2 + L\,dQ_2/dt$$

$$Q_2 - Q_D = C\,dP_3/dt \quad (1)$$

In the transmission line model, the state variables are the current through each of the inductors 36 as well as the voltage across each of the capacitors 38. In the present invention, the ground 46 of the transmission line model 32 is assumed to be zero such that the voltage across each of the capacitors represents the voltage at nodes $P_1$, $P_2$, and $P_3$. As previously indicated, the voltage in the transmission line model corresponds to pressure in the arterial pulse wave representation. Thus, solving for the parameters of the transmission line model and specifically the resistance of the resistors 40, results in a blood viscosity measurement.

In matrix form, these equations are given by:

$$\begin{bmatrix} \dot{P}_1 \\ \dot{Q}_1 \\ \dot{P}_2 \\ \dot{Q}_2 \\ \dot{P}_3 \end{bmatrix} = \begin{bmatrix} 0 & -1/C & 0 & 0 & 0 \\ 1/L & -R/L & -1/L & 0 & 0 \\ 0 & 1/C & 0 & -1/C & 0 \\ 0 & 0 & 1/L & -R/L & -1/L \\ 0 & 0 & 0 & 1/C & 0 \end{bmatrix} \begin{bmatrix} P_1 \\ Q_1 \\ P_2 \\ Q_2 \\ P_3 \end{bmatrix} + \begin{bmatrix} 1/C & 0 \\ 0 & 0 \\ 0 & 0 \\ 0 & 0 \\ 0 & -1/C \end{bmatrix} \begin{bmatrix} Q_P \\ Q_D \end{bmatrix} \quad (2)$$

where the notation $\dot{P}$ is used to denote the first derivative of P with respect to time. As will be appreciated by one skilled in the art, in certain embodiments, equation (2) may be of higher order (involving a larger number of state variables) for computing the blood viscosity by the present technique. Defining the vector of state variables $x = [P_1\ Q_1\ P_2\ Q_2\ P_3]^T$, one may write this as $$\dot{x} = Ax + B \begin{bmatrix} Q_P \\ Q_D \end{bmatrix} \quad (3)$$

where the matrices A and B are defined conventionally. Equation (3) gives a continuous-time expression for the transmission line model. The signal processing algorithm operates in discrete time, since the proposed measurements are intrinsically discrete time. In order to convert Equation (3) into an equivalent discrete-time model, a new state feedback matrix G is defined, which is the state transition matrix of the continuous system over the sample period. An input matrix F is defined that is equivalent to the effect of a constant input signal over the sample period:

$$x(k+1) = e^{AT}x(k) + \left(\int_0^T e^{At} dt\right) B \begin{bmatrix} Q_P(k) \\ Q_D(k) \end{bmatrix}$$
$$= Gx(k) + F \begin{bmatrix} Q_P(k) \\ Q_D(k) \end{bmatrix} \quad (4)$$

This well-known approach to discretization of a continuous time linear system represents a delay-free, zero-order hold assumption for the digitization of the driving signals. This is equivalent to representing the driving input signal by a piecewise constant approximation. Other digitization models can also be employed, such as a first-order hold, which represents the input signal as piecewise linear. Higher order hold models may be required at lower sample rates. Although the effects of quantization of the flow measurements are not included in this model, these effects can simply be considered as part of the additive observation noise.

The basic operation of the ladder network of the transmission line model is to integrate the two flow signals to get a time-varying volume estimate, and to scale that using the compliance (C) and measured pressure (P) to obtain a resistance (R) estimate, which is then used to compute the blood viscosity. For linear compliance, the relationship between the cross-sectional area (A) of the lumen and the pressure (P) is simply $A=CP+A_0$, and in a uniform tube, the volume (V) is simply Al, for a segment of length l. The series resistors 40, representing blood viscosity, are very important in implementing the low-pass frequency response characteristic that performs the integration.

In addition, the network implements a delay for the flow signals. Because of this delay, blood observed entering the system at a given time at one end is canceled by blood leaving the system at a later time at the other end, with the interval determined by the implemented delay. This is true for the forward flow wave and also for the reflected, or retrograde, flow wave. When the delay does not match the actual delay in the system, the flow is cancelled either too soon or too late, with the result that the pressures are wrong. The phase velocity of the network depends on the product LC.

Most of the parameters of the ladder network 34 may be obtained from ultrasound and blood pressure cuff measurements. The compliance is defined as the rate of change of area with respect to the pressure and is given as:

$$C = \frac{dA}{dP} \quad (5)$$

The area waveform obtained by ultrasound will be scaled using the compliance estimated from the max, min and mean pressures derived from the cuff to produce an estimated pressure waveform, sampled at a high rate. Since the compliance is known to change with pressure, a pressure-varying value of compliance can be used in the transmission line model. The blood mass/inertia parameter, L, is given by $$L = \frac{\rho}{\pi r^2} \quad (6)$$

which can be measured using only the arterial lumen radius and the known density of blood. The serial resistance is given by:

$$R = \frac{\eta a}{2\pi r^3} = \frac{8\eta}{\pi r^4} \quad (7)$$

where $\eta$ is the viscosity of blood. An adaptive process, described in detail below, can be used to adjust the viscosity until the model is correct.

As will be appreciated by one skilled in the art, when additional measurements located between the two ultrasound patch probes 20 and 22 of FIG. 1 are available, they cannot be utilized as sources since that would have the effect of decoupling the sections of the model proximal and distal to the new source. Additionally, the scaled area measurements at the two end measurement sites also need to be incorporated into the model.

In such situations, the estimation procedure may employ a Kalman filter and use the new observations as measurements of state variables of the transmission line model, while retaining the original two measurements as system inputs. Using this approach, both flow and pressure waveforms can be incorporated, as available. Each measurement must correspond to a state variable that best represents its distance from the two ends of the model, defined by the two driving flow measurements.

The Kalman filter algorithm is composed of three main operations, which together recursively update the system state and its covariance matrix, which in turn determines the relative weight given to the observations as opposed to that given to the current state estimates. In the general form of the Kalman filter, the state update mechanism is taken to occur with additive noise. In accordance with the present invention, process noise is omitted from the model, or equivalently, the covariance matrix is set to zero.

In order to accommodate interior observation sites, an observation matrix H is designed that specifies the observed state variables. In general, H has the same number of columns as the dimension of the state vector and the number of rows is equal to the number of additional observations. In each row, there is only one non-zero entry, which is unity if the measured state variable is a flow and C if the state variable is a pressure and the measurement is an area. The observation is then defined as:

$$z(k) = Hx(k) + v_k \quad (8)$$

where $v_k$ is an observation noise vector with covariance matrix $R = \text{diag}(\sigma_n)$. The components of z(k) are either noisy flow measurements or noisy scaled area (that is, pressure) measurements.

At the start of every iteration of the Kalman algorithm, it is assumed that an estimate of the current state vector denoted by $\hat{x}(k)$, is known, and its (time-varying) covariance matrix, denoted $P(k)$, is also known. On the initial iteration, $P(1)$ is set to a diagonal matrix with large entries, to represent the initial uncertainty in the state estimate. From the state and observation covariance matrices, the Kalman gain is computed, given by $$K(k) = P(k)H^T(HP(k)H^T + R)^{-1} \quad (9)$$

The innovations sequence is simply the difference between the observation and the observation that would be predicted by the current state vector. The Kalman gain matrix computed in Equation (9) is used to weight the innovations sequence to produce an updated estimate of the state vector at the $k^{th}$ sample time.

$$\hat{x}(k) = \hat{x}(k) + K(k)(z(k) - H\hat{x}(k)) \quad (10)$$

Note that this equation replaces the current state vector by a weighted sum of itself and the observation.

The third and last step in the Kalman algorithm is to project the state vector and its covariance matrix to the next sample time:

$$\hat{x}(k+1) = G\hat{x}(k) + F\begin{bmatrix} Q_P(k) \\ Q_D(k) \end{bmatrix} \quad (11a)$$

$$P(k+1) = G[(I - K(k)H)P(k)]G^T \quad (11b)$$

The effect of the Kalman filter is to replace the observed state variables at every step with a weighted average of their observed and predicted values. In the steady state, the weights depend to a large extent on the value of the noise variance on the main diagonal of R.

It is well-known that the actual compliance of arteries is not constant. The artery compliance is the slope of the transfer characteristic between pressure and the cross-sectional area of the vessel lumen. This characteristic is nonlinear because of the collagen fibers in the arterial wall, which are relaxed until a certain stage of the distension of the vessel, and then become taut, decreasing the elasticity. Thus, the compliance can be considered to be dependent on pressure. This nonlinear relationship can be represented by a piecewise linear relationship such that the compliance is different in a number of disjoint pressure ranges. This kind of pressure-dependent compliance can easily be incorporated into the time-domain approach above.

The pressure/area relationship has been modeled in the prior literature as an exponential. This transfer function was applied to a Windkessel model of the entire arterial system as seen from the aorta, and was found to have some advantages in terms of predicting the shape of observed pressure waveforms.

In the present model, the compliance enters into the definition of G, F and H. In order to implement pressure-dependent compliance, a different set of matrices must be implemented for every distinct pressure interval over which the compliance is constant. Equations (9), (10) and (11) are then executed using that set of matrices that is associated with the estimated pressure at step (k−1).

There are several features of flow estimation using ultrasound that must be kept in mind when implementing the present technique. Volumetric flow estimation proceeds in the same way as ultrasound color flow mapping over a limited sector. Color flow mapping is a standard feature of most diagnostic ultrasound devices that estimates blood velocity at a number of locations on the image plane by computing the mean frequency of the spectrum of the returned ultrasound signal. This mean frequency corresponds to a mean Doppler shift induced by the moving blood. This measurement process involves insonifying a volume from which a blood velocity is desired, and this occurs from three to sixteen times for every estimate. This is done along several ultrasound A-lines. Once a set of blood velocity estimates is available at a number of locations covering the vessel lumen, the estimates are all multiplied by the area to which they individually apply and the products are summed. This implements an approximate integration over the lumen and the result is a volumetric flow.

However, ultrasound flow mapping can produce blood velocity estimates that are highly biased down from the true blood velocity if the ultrasound return contains significant energy from stationary tissue reflections. For this reason, the data used to compute the mean frequency estimates (the Doppler shifts) is typically high-pass filtered. This means that very low flows, such as might be encountered during diastole in a peripheral artery, may be missed. Since the majority of the flow undoubtedly occurs when the blood velocity is high, this may not be a major problem, but still, some portion of the flow is bound to be neglected due to this effect.

Another effect that can change the performance of the blood viscosity estimation is the dependence of the ultrasound velocity measurement on angle. The measured phase change is indicative of the projection of the blood velocity vector on the ultrasound line. If the various flow measurements are based on different Doppler angles, they can be incommensurate. The lossless circuit of FIG. 2 requires that positive current entering the system at the proximal source 42 be canceled by negative current entering the system at the distal source 44 after some delay. If the angles of the two ultrasound lines are different, this cancellation will not take place, and the blood pressure will not be correctly computed. Note that if the ultrasound patch probes 20, 22 of FIG. 1 are mechanically connected to each other by a rigid structure, identical insonification angles are easily obtained.

No matter how many ultrasound lines are used to produce the velocity estimates, a new estimate can be computed for every new line, even though it will be highly correlated with the last such estimate. This means that a new volumetric flow estimate can be obtained for every frame. That is, the frame rate and volumetric flow sample rate are the same. The frame rate should be maximized by using only the minimum number of ultrasound lines required to cover the artery.

In the above discussion of the parameters of the transmission line model, it was noted that not all of the important parameters were directly observable using ultrasound. In particular, the blood viscosity represents a degree of freedom not directly observable.

A data-adaptive processing operation can be utilized to find the undetermined free parameters of the model. This method, however, requires that at least one additional measurement be made, over and above the two required flow measurements described previously.

Many adaptive filters operate by minimizing a prediction error energy ($E_p$). In general, a prediction error is the error between the response of the filter to a known input and the response of the real system to that input. This is a well-known principle in spectrum estimation and system identification. In accordance with the aspects of the present technique, this approach is employed to indicate the degree of agreement between the parameters of the transmission line model and the state of the physical system.

For this purpose one may use the model of the observations defined in Equation (8) in connection with the Kalman filter approach. The prediction error power at the $k^{th}$ sample is given by the squared norm of the $k^{th}$ element of the innovations sequence, and the prediction error energy is proportional to the prediction error power summed over some fixed period of time:

$$E_p = T_s \sum_{k=k_0}^{k_1} |z(k) - H\hat{x}(k)|^2 \quad (12)$$

where $T_s$ is the sample period.

The adaptive filter works by applying multiple sets of parameters to the data in parallel over a fixed period of time, and computing $E_p$ for each. The parameter producing the lowest prediction error energy is taken to be the correct value from among the set of trial parameters. This is a well-known, sub-optimal approximation to the optimal approach of computing conditional probabilities for each trial parameter. (See R. G. Brown, Introduction to Random Signal Analysis and Kalman Filtering, John Wiley and Sons, 1983, pp. 302-307.) Because the observed waveforms will be limited in duration, the filter algorithm will be performed over that same record over and over again until the prediction error is minimized.

The parameter that will be varied by this adaptation will be η, since the L parameter and the other components of the C and R parameters can be measured using ultrasound. It is also possible to limit adaptation of these parameters to a region around the nominal value of η.

Adaptation of the system parameters using prediction error is consistent with incorporation of the additional measurements using the Kalman filter. All that is required is the execution of the operations given by equations (9), (10) and (11b) in addition to the normal operation given above. There is a potential problem in this approach, however. To the extent that the observation used to generate prediction error updates the state variable to which is compared, the sensitivity of the prediction error to model errors will be reduced. The degree to which the observations update the state variables is controlled by the noise variance specified in the R matrix; thus, adaptive Kalman filter operation will require that the noise variance is set to a high level.

Figure 3:
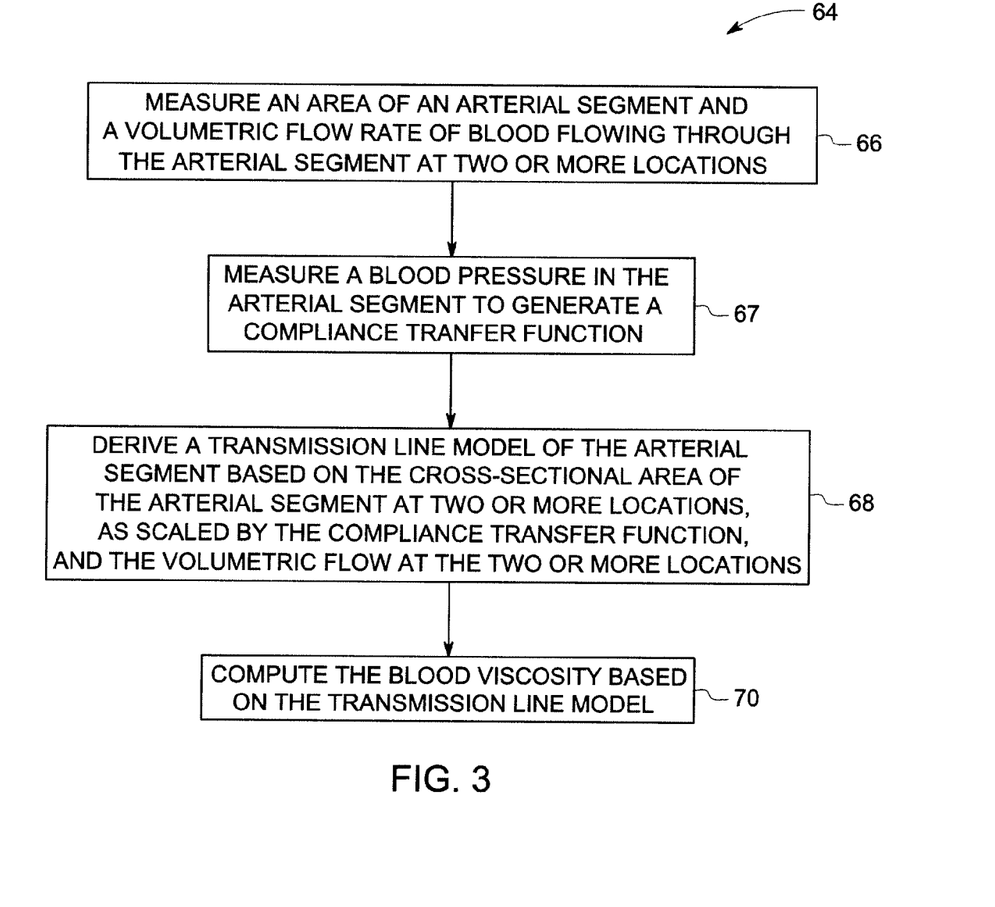
FIG. 3 is a flowchart depicting an exemplary process for computing or monitoring blood viscosity in accordance with aspects of the present technique.

Referring now to FIG. 3, exemplary control logic 64 for computing or monitoring blood viscosity is depicted via a flowchart in accordance with aspects of the present technique. As illustrated in the flowchart, exemplary control logic 64 includes the steps of measuring a cross sectional area of a arterial segment and a volumetric flow rate of blood flowing through the arterial segment at two or more locations at step 66, measuring a blood pressure in the arterial segment to generate a compliance transfer function at step 67, deriving a transmission line model of the arterial segment based on the cross sectional area of the arterial segment at two or more locations, as scaled by the compliance transfer function, and the volumetric flow rate of blood at the two or more locations at step 68, and computing the blood viscosity based on the transmission line model at step 70.

The ultrasound input measurements at step 66 and pressure measurement at step 67 are all transferred to a transmission line simulator (processor 14). The transmission line simulator utilizes the ultrasound input measurements along with the measured pressure waveform to carry out the calculation steps previously described. The transmission line simulator includes the Kalman filtering as well as the state variable formulas to generate the blood viscosity estimates, which is then displayed to the user.

Figure 4:
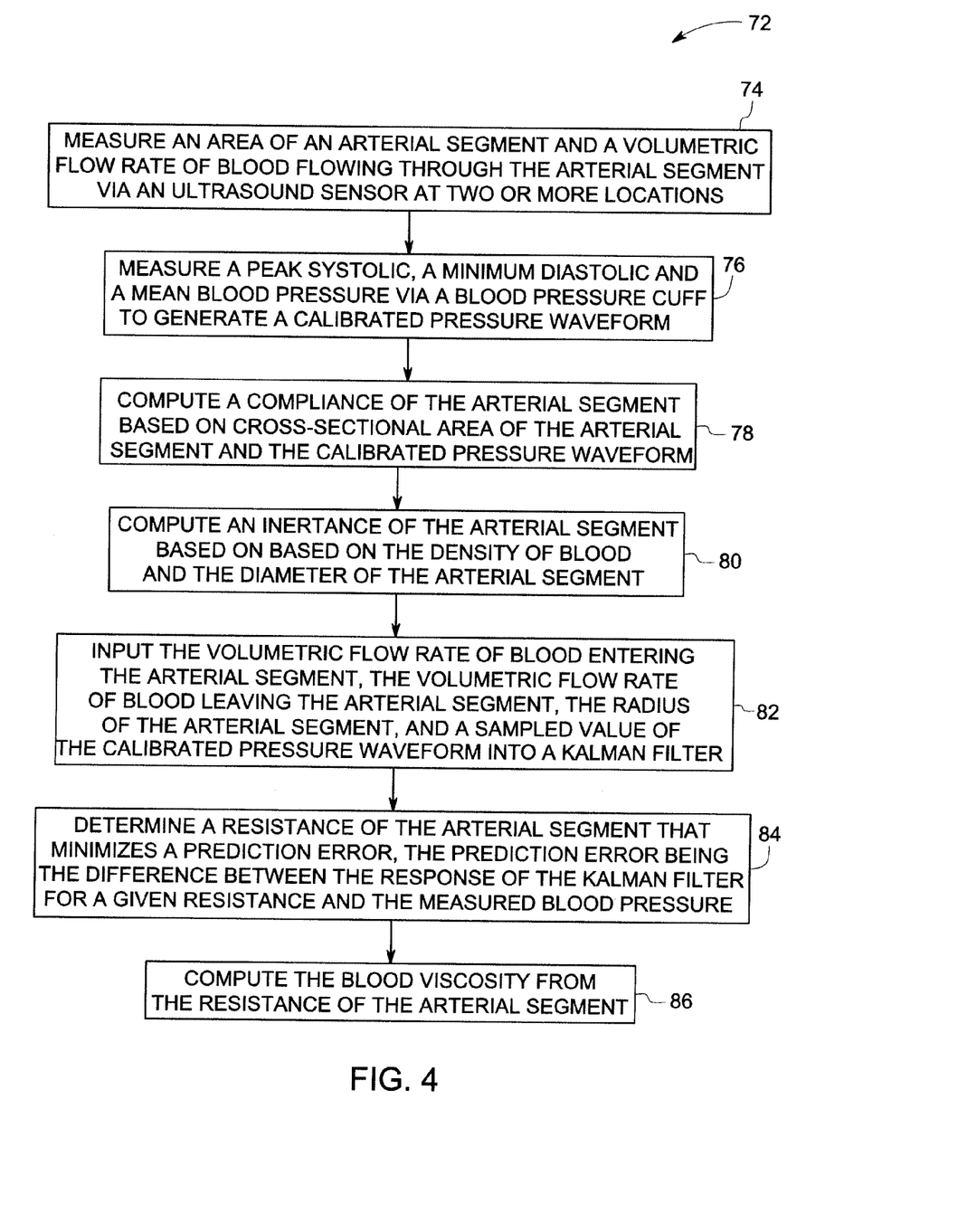
FIG. 4 is a flowchart depicting the exemplary process of FIG. 3, in greater detail and in accordance with aspect of the present technique.

By means of further example, the blood viscosity computation and measurement technique illustrated in FIG. 3 may further be elaborated as shown in FIG. 4. As illustrated in the flowchart, the control logic 72 set forth in FIG. 4, includes the steps of measuring a cross sectional area or a diameter of a arterial segment and a volumetric flow rate of blood flowing through the arterial segment via an ultrasound sensor at two or more locations at step 74, measuring a peak systolic, a minimum diastolic and a mean blood pressure via a blood pressure cuff to generate a calibrated pressure waveform at step 76, computing a compliance of the arterial segment based on the cross-sectional area of the arterial segment and the calibrated pressure waveform at step 78, and computing an inertance of the arterial segment based on a known density of blood and the diameter of the arterial segment at step 80. It should be noted that the cross-sectional area may be computed from the diameter of the arterial segment and vice versa. The control logic 72 further includes the steps of inputting the volumetric flow rate of blood entering the arterial segment, the volumetric flow rate of blood leaving the arterial segment, the cross sectional area or the diameter of the arterial segment, which is scaled to form a sampled value of the calibrated pressure waveform, into a Kalman filter at step 82, determining a resistance of the arterial segment that minimizes a prediction error at step 84, and computing the blood viscosity from the resistance of the arterial segment at step 86. It should be noted that the prediction error is the difference between the response of the Kalman filter for a given resistance and the measured state variables. Further, it should be noted that the sampled value of the calibrated pressure waveform is generated by sampling the calibrated pressure waveform at a rate equal to a rate of measurement of the volumetric flow rate of blood. As will be appreciated by one skilled in the art, determining the resistance of the arterial segment that minimizes the prediction error at step 84 comprises providing multiple estimates of the resistance, calculating the prediction error for each of the estimates, selecting the estimate that results in the smallest prediction error.

It should be noted that step 74 may include measuring a mean radius or diameter of the arterial segment or measuring a time varying radius or diameter of the arterial segment. Further, the compliance of the arterial segment (the "C" of the transmission line) is estimated at step 78 by computing an approximation to the derivative of arterial area with respect to pressure, using the area measurements from ultrasound and the pressure measurements from the cuff. A piecewise linear model of the compliance is computed at this step. Similarly, the inertance of the arterial segment (the "L" of the transmission line) is estimated at step 80 using equation (6) and substituting in the known density of blood and the measured arterial lumen radius. This may either use the mean radius to produce a constant value of L or use the time-varying radius to produce a time-varying estimate of L.

Additionally, it should be noted that if a mean value of L was estimated in step 80, then a mean value of R is computed at step 84. Alternatively, if a time-varying value of L was estimated in step 80, then a time-varying value of R over some definite portion of the measured data is computed at step 84. Finally, the value of the blood viscosity is computed from equation 9 at step 86. If a constant value of R was computed in step 84, then the mean value of the radius is used in the present computation. If R was computed as a waveform at step 84, the blood viscosity is computed as that constant that minimizes the integrated squared error (E) give by $$E = \int_T \left(R(t) - \frac{8\eta}{\pi r^4(t)}\right)^2 dt \quad (13)$$

where R(t) is the time varying resistance, 2r(t) is the time varying diameter, and the integration is over the duration (T) of the period for which R(t) is estimated.

As will be appreciated by one skilled in the art, the techniques described in the various embodiments discussed above provides a continuous, non-invasive viscosity measurement by employing ultrasound patch probes placed on the skin of the patient and a standard oscillometric blood pressure cuff. The continuous, non-invasive measurement also enables monitoring of this parameter for a patient.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method, performed by a processor, the method comprising:
   measuring a cross sectional area of an arterial segment and a volumetric flow rate of blood flowing through the arterial segment at two or more locations;
   estimating a compliance transfer function for the arterial segment by the processor using measured minimum, maximum and mean values of blood pressure;
   deriving a transmission line model of the arterial segment by the processor based on the cross sectional area of the arterial segment at the two or more locations as scaled by the compliance transfer function and the volumetric flow rate of blood at the two or more locations; and
   computing, by the processor, the blood viscosity based on the transmission line model.

2. The method of claim 1, further comprising positioning an ultrasound sensor aligned with the arterial segment at each of the two or more locations to measure the cross sectional area of the arterial segment and the volumetric flow rate of blood at the respective location.

3. The method of claim 1, wherein the transmission line model includes a plurality of RLC ladder network stages between an input current source and an output current source, wherein the input current source is a volumetric flow rate of blood entering the arterial segment and the output current source is a volumetric flow rate of blood leaving the arterial segment.

4. The method of claim 3, wherein each of the plurality of RLC ladder network stages includes a series resistor, an inductor, and a capacitor, wherein resistance of the series resistor is analogous to the resistance of the arterial segment and is given by $R=8\eta/\pi r^4$, inductance of the inductor is analogous to the inertance of the blood arterial segment and is given by $L=\rho/\pi r^2$, and capacitance of the capacitor is analogous to the compliance of the arterial segment and is given by $C=dA/dP$, wherein $\eta$ is the blood viscosity, $\rho$ is the blood density, r is the radius of the arterial segment, A is the cross sectional area of the arterial segment, and P is the blood pressure.

5. The method of claim 1, wherein the measuring the cross sectional area of the arterial segment comprises measuring a diameter of the arterial segment and computing the cross sectional area based on the diameter.

6. The method of claim 1, measuring a blood pressure in the arterial segment comprises measuring the blood pressure via a blood pressure cuff.

7. The method of claim 1, further comprising computing inductance and capacitance of the transmission line model based on a known density of blood, a measured or computed diameter or cross sectional area of the arterial segment, and the measured blood pressure waveform.

8. The method of claim 1, wherein computing the blood viscosity based on the transmission line model comprises solving the transmission line model to determine resistance of the transmission line model, and computing the blood viscosity from the resistance.

9. The method of claim 8, wherein solving the transmission line model comprises:
   developing a series of state variable equations based on the transmission line model;
   inputting the volumetric flow rate of blood entering the arterial segment, the volumetric flow rate of blood leaving the arterial segment, and the cross sectional area of the arterial segment into a Kalman filter; and
   utilizing the Kalman filter to estimate state variables of the transmission line model, wherein the state variables include a capacitor voltage representative of blood pressure for each node in the transmission line model.

10. The method of claim 9, further comprising initializing the state variables using the measured blood pressure.

11. The method of claim 10, further comprising
   comparing a current value of each of the state variables with an initialized value of the respective state variable; and
   re-initializing the respective state variable when the current value differs from the initialized value by more than a pre-determined threshold value.

12. The method of claim 9, wherein the state variable equations include a resistive parameter, the method further comprising:
   providing multiple, separate estimates for the value of the resistive parameter;
   calculating a prediction error for each of the estimates, wherein the prediction error is the difference between the response of the Kalman filter for the provided estimate and the measured blood pressure;
   selecting the estimate of the resistive parameter that results in the smallest prediction error; and
   utilizing the selected estimate to compute the blood viscosity.

13. The method of claim 9, further comprising
   continuously measuring the cross sectional area of the arterial segment and the volumetric flow rate of blood flowing through the arterial segment at the two or more locations;
   continuously updating the state variable equation with most recent measurements of the cross sectional area, and the incoming and the outgoing volumetric flow rates, such that the Kalman filter provides a continuous, real time blood viscosity measurement.

14. A method, performed by a processor, the method comprising:
   measuring a cross sectional area of an arterial segment and a volumetric flow rate of blood flowing through the arterial segment via an ultrasound sensor at two or more locations;
   estimating a compliance transfer function for the arterial segment by the processor using measured minimum, maximum and mean values of blood pressure;
   deriving a transmission line model of the arterial segment by the processor, the transmission line model comprising a plurality of RLC ladder network stages between an input current source and an output current source, each of the plurality of RLC ladder network stages further comprising a series resistor, an inductor, and a capacitor, wherein the input current source is a volumetric flow rate of blood entering the arterial segment, the output current source is a volumetric flow rate of blood leaving the arterial segment, resistance of the series resistor is analogous to the resistance of the arterial segment and is given by $R=8\eta/\pi r^4$, inductance of the inductor is analogous to the inertance of the arterial segment and is given by $L=\rho/\pi r^2$, and capacitance of the capacitor is analogous to the compliance of the arterial segment and is given by $C=dA/dP$, and wherein $\eta$ is the blood viscosity, $\rho$ is the blood density, r is the radius of the arterial segment, A is the cross sectional area of the arterial segment, and P is the blood pressure;

solving the transmission line model to determine resistance of each of the series resistors; and, computing, by the processor, the blood viscosity from the resistance.

15. A method, performed by a processor, the method comprising:

measuring a cross sectional area or a diameter of an arterial segment and a volumetric flow rate of blood flowing through the arterial segment via an ultrasound sensor at two or more locations;

measuring a peak systolic, a minimum diastolic and a mean blood pressure via a blood pressure cuff to generate a calibrated pressure waveform;

computing, by the processor, an inertance of the arterial segment based on based on a known density of blood and the diameter of the arterial segment;

inputting the volumetric flow rate of blood entering the arterial segment, the volumetric flow rate of blood leaving the arterial segment, and the cross sectional area or the diameter of the arterial segment into a Kalman filter;

determining a resistance of the arterial segment that minimizes a prediction error, the prediction error being the difference between the response of the Kalman filter for a given resistance and the measured blood pressure;

computing, by the processor, the blood viscosity from the resistance of the arterial segment.

16. The method of claim 15, wherein determining the resistance of the arterial segment that minimizes the prediction error comprises providing multiple estimates of the resistance, calculating the prediction error for each of the estimates, selecting the estimate that results in the smallest prediction error.

17. The method of claim 15, wherein measuring the diameter, computing the inertance, and determining the resistance of the arterial segment comprises measuring mean diameter, computing mean inertance based on the mean diameter, and determining mean resistance based on the mean inertance.

18. The method of claim 15, wherein measuring the diameter, computing the inertance, and determining the resistance of the arterial segment comprises measuring time varying diameter, computing time varying inertance based on the time varying diameter, and determining time varying resistance based on the time varying inertance.

19. The method of claim 18, wherein computing the blood viscosity from the time varying resistance comprises computing the blood viscosity that minimizes the integrated square (E) error given by $$E = \int_T \left(R(t) - \frac{8\eta}{\pi r^4(t)}\right)^2 dt,$$

wherein R(t) is the time varying resistance, 2r(t) is the time varying diameter, $\eta$ is the blood viscosity, and T is the duration of the period for which R(t) is measured.

20. A blood viscosity measurement and monitoring system, comprising:

two or more ultrasound sensors configured to measure a cross sectional area of an arterial segment and a volumetric flow rate of blood flowing through the arterial segment at two or more locations respectively; and a blood pressure cuff configured to measure a blood pressure in the arterial segment to generate a calibrated pressure waveform;

a processor coupled to the two or more ultrasound sensors and the blood pressure cuff and configured to derive a transmission line model of the arterial segment based on the cross sectional area of the arterial segment and the volumetric flow rate of blood at the two or more locations and the calibrated pressure waveform, and to compute the blood viscosity based on the transmission line model.

21. The system of claim 20, wherein the transmission line model includes a plurality of RLC ladder network stages between an input current source and an output current source, wherein the input current source is a volumetric flow rate of blood entering the arterial segment and the output current source is a volumetric flow rate of blood leaving the arterial segment.

22. The system of claim 21, wherein each of the plurality of RLC ladder network stages includes a series resistor, an inductor, and a capacitor, wherein resistance of the series resistor is analogous to the resistance of the arterial segment and is given by $R=8\eta/\pi r^4$, inductance of the inductor is analogous to the inertance of the blood arterial segment and is given by $L=\rho/\pi r^2$, and capacitance of the capacitor is analogous to the compliance of the arterial segment and is given by $C=dA/dP$, wherein $\eta$ is the blood viscosity, $\rho$ is the blood density, r is the radius of the arterial segment, A is the cross sectional area of the arterial segment, and P is the blood pressure.

23. The system of claim 20, wherein the processor is further configured to compute inductance and capacitance of the transmission line model based on a known density of blood, a measured or computed diameter or cross sectional area of the arterial segment, and the measured blood pressure waveform.

24. The system of claim 20, wherein the processor is configured to compute the blood viscosity by solving the transmission line model to determine resistance of the transmission line model, and computing the blood viscosity from the resistance.

25. The system of claim 24, wherein the processor is configured to solve the transmission line model by developing a series of state variable equations based on the transmission line model, and utilizing the Kalman filter to estimate state variables of the transmission line model, wherein the state variables include a capacitor voltage representative of blood pressure for each node in the transmission line model.

26. The system of claim 25, wherein the processor is configured to initialize the state variables using the measured blood pressure.

27. The system of claim 26, wherein the processor is configured to compare a current value of each of the state variables with an initialized value of the respective state variable, and to re-initialize the respective state variable when the current value differs from the initialized value by more than a pre-determined threshold value.

28. The system of claim 25, wherein the state variable equations include a resistive parameter and the processor is further configured to provide multiple, separate estimates for the value of the resistive parameter, to calculate a prediction error for each of the estimates, to select the estimate of the resistive parameter that results in the smallest prediction error; and to utilize the selected estimate to compute the blood viscosity, wherein the prediction error is the difference between the response of the Kalman filter for the provided estimate and the measured blood pressure.

29. The system of claim 25, wherein the two or more ultrasound sensors are further configured to continuously measure the cross sectional area of the arterial segment and the volumetric flow rate of blood flowing through the arterial segment at two or more locations respectively, and the processor is further configured to continuously update the state variable equation with most recent measurements of the cross sectional area, and the incoming and the outgoing volumetric flow rates, such that the Kalman filter provides a continuous, real time blood viscosity measurement.

* * * * *